US006846769B2

(12) United States Patent
Arndt-Rosenau et al.

(10) Patent No.: US 6,846,769 B2
(45) Date of Patent: Jan. 25, 2005

(54) VANADIUM-IMIDO-PHOSPHORANEIMINATO COMPLEXES FOR THE POLYMERIZATION OF OLEFINS

(75) Inventors: Michael Arndt-Rosenau, Dormagen (DE); Martin Hoch, Heinsberg (DE); Jörg Sundermeyer, Marburg (DE); Jennifer Kipke, Mannheim (DE); Martin Lemke, Niederweimer (DE)

(73) Assignee: Bayer Aktiengesellschaft, Leverkusen (DE)

(*) Notice: Subject to any disclaimer, the term of this patent is extended or adjusted under 35 U.S.C. 154(b) by 107 days.

(21) Appl. No.: 10/216,573

(22) Filed: Aug. 9, 2002

(65) Prior Publication Data

US 2003/0114675 A1 Jun. 19, 2003

(30) Foreign Application Priority Data

Aug. 16, 2001 (DE) .......................... 101 40 202

(51) Int. Cl.$^7$ .............................. B01J 31/24; B01J 31/00

(52) U.S. Cl. ...................... 502/103; 502/123; 502/121; 526/139; 526/141

(58) Field of Search ........................ 502/103, 123, 502/121; 526/139, 141

(56) References Cited

U.S. PATENT DOCUMENTS

| | | | | |
|---|---|---|---|---|
| 5,086,023 A | * | 2/1992 | Smith ........................ | 502/103 |
| 5,364,916 A | | 11/1994 | Renkema et al. ........... | 532/161 |
| 5,688,733 A | | 11/1997 | Renkema et al. ........... | 502/103 |
| 5,965,677 A | * | 10/1999 | Stephan et al. ............. | 526/129 |

FOREIGN PATENT DOCUMENTS

| | | | |
|---|---|---|---|
| WO | 00/05237 | | 2/2000 |
| WO | WO 00/05237 | * | 2/2000 |

OTHER PUBLICATIONS

Hawkeswood et al. Synthesis and Characterization of Vanadium (V)–Phosphinimide Complex, Inorganic Chemistry, 42, 5429–5433(2003).*

Olms, Chem. Ber. 124, 2655–2661 (1991).*

Enzyklopädie der technischen Chemie, vol. 24, (date unavailable), pp. 575–578, (Zeolites) Zeolithe by Dr. Manfred Mengel.

Enzyklopädie der technischen Chemie, vol. 23, (date unavailable), pp. 311–326, (Clays) T.on und Tonminerale by Prof. Dr. Gerhard Lagaly and Dr. Rudlof Fahn.

Enzyklopädie der technischen Chemie, vol. 14, (date unavailable), pp. 633–651, (carbon blacks) Kohlenstoff.

Enzyklopädie der technischen Chemie, vol. 21, (date unavailable), pp. 439–476, (silica gels) Siliciumdioxid by Dr. R. Weiss et al.

Applied Optics, vol. 11, No. 2, Feb. 1972, pp. 265–268, Particle Size Analyzer by J. Cornillault.

Journal of Colloid and Interface Science, vol. 78, No. 1, Nov. 1980, pp. 31–36, Total Porosity of High–Pore–Volume Silicas by Liquid Adsorption by M. P. McDaniel and T. D. Hottovy.

Z. Naturforsch. B: Anorg. Chem., Org. Chem. 41B(2), (month unavailable) 1986, pp. 185–190, tert–Butylimino–σ–Organovanadium(V)–Verbindungen Darstellung und NMR–spektroskopische und NMR–spektroskopische Untersuchungen by F. Preuss und H. Becker.

Coordination Chemistry Reviews, 182, (month unavailable) 1999, pp. 19–65, Phosphoraneiminato complexes of transition metals by K. Dehnicke, M. Krieger and W. Massa.

J. Am. Chem. Soc., (month unavailable) 1987, 109, pp. 7408–7416, Complexes of (Arylimido) vanadium(V). Synthetic, Structural, Spectroscopic, and Theoretical Studies of V(Ntol)Cl$_3$ and Derivatives by D. D. Devore, J. D. Lichtenhan, F. Takusagawa and E. A. Maatta.

Z. Naturforsch, 44b, (month unavailable) 1989, pp. 35–40, Neue Übergangsmetallkomplexe mit dem Liganden Me$_2$S(O)=NPPh$_2$=N– by H. W. Roesky, F. Schrumpf und M. Noltemeyer.

Inorg. Chem., (month unavailable) 1993, 32, pp. 5102–5104, Oxo Fluorides of Titanium and Vanadium, Preparation and Crystal Structures of [Cp*TiF($\mu$–O)]$_4$ and OVF$_2$N=PPh$_3$ by H. W. Roesky, I. Leichtweis, and M. Noltemeyer.

Inorg. Chem., (month unavailable) 1984, 23, pp. 2560–2561, Preparation, Chemistry, and $^{51}$V NMR Spectroscopy of (p–Tolylimido)vanadium(v) Complexes by E. A. Maatta.

Journal of Organometallic Chemistry, 591, (month unavailable) 1999, pp. 78–87, Transition metal imido catalysts for ethylene polymerisation by M. P. Coles et al.

Journal of Organometallic Chemistry, 497, (month unavailable) 1995, pp. 161–170, Alkylation and reductive dimerization of half–sandwich imido vanadium dichlorides by J. K. F. Buijink.

Z. Anorg. Allg. Chem., (month unavailable) 1999, 625, pp. 901–909, Indenylvanadium(V)– Verbindungen Darstellung, Struktur und NMR–spektroskopische Untersuchungen by F. Preuss.

Journal of Organometallic Chemistry, 584, (month unavailable) 1999, pp. 200–205, Carbodiimide metathesis catalyzed by vanadium oxo and imido complexes via imido transfer by K. R. Birdwhistell, J. Lanza and J. Pasos.

(List continued on next page.)

*Primary Examiner*—Ling-Sui Choi
(74) *Attorney, Agent, or Firm*—Godfried R. Akorli; Jennifer R. Seng

(57) ABSTRACT

The present invention relates to vanadium-imido-phosphoraneiminato compounds, to compositions containing vanadium-imido-phosphoraneiminato compounds, which compositions are suitable especially as catalysts for the polymerization of olefins, especially for ethylene/propylene or ethylene/α-olefin copolymerization and the terpolymerization of those monomers with dienes.

3 Claims, No Drawings

OTHER PUBLICATIONS

Transition Met. Chem., 4, pp. 249–251, (month unavailable) 1979, Azido– and Phosphiniminato– Complexes of Titanium and Vanadium by R. Choukroun, D. Gervais and J. R. Dilworth.

J. Chem. Soc. Dalton Trans., (month unavailable) 1993, pp. 3609–3617, Compounds with Vanadium–Nitrogen and Vanadium–Oxygen Multiple Bonds by A. Hills, D. L. Hughes, G. J. Leigh and R. P. Alcón.

Z. Anorg. Allg. Chem., 374(3), (month unavailable) 1970, pp. 291–296, Über die Darstellung von Verbindungen des typs $Cl_3V-NR$ by Von Adolf Slawisch.

Z. Naturforsch, B: Chem. Soc., 56(3), (month unavailable) 2001, pp. 255–262, Darstellung, Reaktionen un $^{57}$V–NMR–spektroskopische Untersuchungen der Imidovanadium(V)–trichloride: $RN=VCl_3$ (R=H, $SiMe_3$, Alkyl) by F. Preuss et al.

A. Anorg. Allg. Chem., 609, (month unavailable) 1997, pp. 45–50, Darstellung und NMR–spektroskopie Utersuchungen der tert–Butylimino–cyclopentadienylvanadium(V)–Verbindungen $^tC^4H^9N=VCPX_2$ (X=SR, $SeC_6H_5$, Br, I) by F. Preuss et al.

Z. Naturforsch, B: Chem Sci., 55(1), (Month unavailable) 2000, pp. 1–4, Alkylsubstitutuierfe Cyclopentadienylvanadium(v)–Komplexe: $^1C_4H_9N=VCp^RCl_2$ by F. Preuss et al.

Z. Naturforsch. B25(3), (month unavailable) 1970, p. 321, Zur Darstellung von Vanadiuniuminen: $Cl_6P_4N_4(N=VCl_3)_2$ by Slawisch et al.

* cited by examiner

VANADIUM-IMIDO-PHOSPHORANEIMINATO COMPLEXES FOR THE POLYMERIZATION OF OLEFINS

FIELD OF THE INVENTION

The present invention relates to vanadium-imido-phosphoraneiminato compounds and to compositions containing vanadium-imido-phosphoraneiminato compounds, in which compositions are suitable especially as catalysts for the polymerization of olefins, especially for ethylene/propylene or ethylene/α-olefin copolymerization and the terpolymerization of those monomers with dienes.

BACKGROUND OF THE INVENTION

Transition metal imido complexes, especially imido complexes of vanadium, are known from the literature (A. Slawisch, Z. Anorg. Allg. Chem. 374(3) (1970) 291–296; A. Slawisch et al. Z. Naturforsch. B 25(3) (1970), 321; E. A. Maata Inorg. Chem. 23(17) (1984), 2560–2561; F. Preuss et al. Z. Naturforsch., B: Anorg. Chem., Org. Chem. 41B(2) (1986), 185–190; D. Devore et al. J. Am. Chem. Soc. 109 (1987), 7408–7416; F. Preuss et al. Z. Anorg. Allg. Chem. 609 (1992), 45–50; A. Hills et al. J. Chem. Soc., Dalton Trans. 1993, 3609–3617; J.-K. F. Buijink J. Organomet. Chem. 497(1–2) (1995), 161–170; M. P. Coles et al. J. Organomet. Chem. 591(1–2) (1999), 78–87; K. R. Birdswell et al. J. Organomet. Chem. 584(1) (1999), 200–205; F. Preuss et al. Z. Anorg. Allg. Chem. 625 (1999), 901–909; F. Preuss et al. Z. Naturforsch., B: Chem. Sci. 55(1) (2000), 1–4; F. Preuss et al. Z. Naturforsch., B: Chem. Sci. 56(3) (2001), 255–262).

EP-A2-0 518 415 describes vanadium-imidoaryl complexes R—N=VX$_3$, wherein X is a single-bonded ligand, and their use in the preparation of EPDM, an improved incorporation of diene being achieved in comparison with catalysts based on VOCl$_3$. However, those catalysts exhibit markedly lower activities in comparison with VOCl$_3$.

EP-A1-0 532 098 describes vanadium-imidoaryl complexes which are substituted in the ortho-positions of the aryl group, and their use as catalysts for the polymerization of olefins at low Al/V ratios. At high Al/V ratios, identical products having slightly diminished catalytic activities are obtained in comparison with catalysts based on VOCl$_3$.

WO-94/14854-A1 describes vanadium-imidoarylamides as catalysts having high activity for the preparation of EPDM, a dialkyl-substituted aryl group again preferably being used in the imide.

In contrast to sigma-bonded ligands, such as are present in the above-described compounds in addition to the imido group, phosphor-aneiminato groups can act as multi-electron donors and hence, transfer a greater electron density to the central atom (A. W. Johnson et al. "Ylides and Imines of Phosphorous", J. Wiley & Sons (1993), K. Dehnicke et al. Coord. Chem. Rev. 182 (1999), 19–65).

Vanadyl-phosphoraneiminato complexes were described for the first time by R. Choukroun et al. (Trans. Met. Chem. 4 (1979), 249). They synthesized VOCl$_2$(NPPh$_3$), VOCl(NPPh$_3$)$_2$ and VCl$_3$(NPPh$_3$)$_2$. Roesky, et al. (H. W. Roesky et al.; Z. Naturforsch. 44b (1989), 35; H. W. Roesky, et al. Inorg. Chem. 32 (1993), 5102–5104) describe the synthesis of VOCl$_2$(NPPh$_2$NSMe$_2$O) and VOF$_2$(NPPh$_3$).

WO 00/05237 describes the use of transition metal complexes having phosphoraneiminato ligands as catalysts for the polymerization of olefins. Activation with single aluminum alkyls is described as "comparatively weak", and activation by aluminoxane or "ionic activators", such as, for example, trityltetrakis(pentafluorophenyl)borate, is described as markedly better.

SUMMARY OF THE INVENTION

Surprisingly, it has been found that novel vanadium-imino-phosphoraneiminato complexes in combination with aluminum alkyls and aluminum alkyl halides form highly active catalysts for the polymerization of olefins. Activation by simple aluminum alkyls is substantially cheaper than activation by alumoxanes or ionic activators. Inexpensive highly active catalysts permit the economic preparation of polymers with lower catalyst residues, and costly washing and purification steps can thus, be avoided.

The invention accordingly provides vanadium-imido-phosphoraneiminato compounds.

DETAILED DESCRIPTION OF THE INVENTION

Preferred vanadium-imido-phosphoraneiminato compounds correspond to the general formula:

$$R-N=VCl_2(NPR^1R^2R^3) \quad (I)$$

or

$$R-N=VXY(NPR^1R^2R^3) \quad (II),$$

wherein

R represents a $C_1-C_{10}$-alkyl group, a $C_6-C_{14}$-aryl group or a $C_1-C_{10}$-heteroaryl group, wherein X,Y are each independently of the other different or identical monoanionic ligands which may be bonded to one another and/or to the R group of the imide, or its substituents, and/or to the radicals $R^1$, $R^2$, $R^3$ of the iminophosphorane, or wherein X and/or Y is likewise an iminophosphorane having radicals $R^4$, $R^5$, $R^6$ and $R^7$, $R^8$, $R^9$ that can be chosen as desired, wherein $R^1$, $R^2$, $R^3$ and, optionally, $R^4$, $R^5$, $R^6$, $R^7$, $R^8$, $R^9$ are each independently of the others different or identical $C_1-C_{10}$-alkyl, $C_6-C_{14}$-aryl, $C_1-C_{10}$-alkoxy groups which may be bonded to one another and/or to the R group of the imide, or its substituents, and/or to the radicals $R^1$, $R^2$, $R^3$ of the iminophosphorane, or alternatively one or more substituents of the phosphorus are bonded to the phosphorus via heteroatoms Het such as, for example, N, O, S.

The bond between phosphorus and the heteroatom(s) can be single and/or double; in the case of a double bond between the phosphorus and the heteroatom, the phosphorus center carries only one further, single-bonded substituent (in addition to the imido group and the group bonded via the hetero atom). The heteroatom(s) can carry one or more further substituents, which can be selected independently of one another from $C_1-C_{10}$-alkyl, $C_6-C_{14}$-aryl, $C_1-C_{10}$-alkoxy groups. Examples of such compounds are imino-tris(dimethylamino)-phosphorane, imino-bis(dimethylamino)-phenyl-phosphorane, imino-(dimethylamino)-di(n-butyl)-phosphorane, imino-tris(N-anilino)-phosphorane, imino-tris(methoxy)-phosphorane, imino-di(methoxy)-(n-butyl)-phosphorane, imino-(amino)-di(phenyl)-phosphorane.

$C_6-C_{14}$-aryl is to be understood as meaning all mono- or poly-nuclear aryl radicals having from 6 to 14 carbon atoms that are known to the person skilled in the art, such as phenyl, naphthyl, fluorenyl; the aryl group can, moreover, carry further substituents. Suitable substituents are hydrogen, halogen, nitro, $C_1$–$C_{10}$-alkoxy or $C_1$–$C_{10}$-alkyl, as well as $C_6$–$C_{14}$-cycloalkyl or $C_6$–$C_{14}$-aryl, such as bromophenyl, chlorophenyl, toloyl and nitrophenyl.

$C_1$–$C_{10}$-heteroaryl is to be understood as meaning all mono- or poly-nuclear heterocyclic aromatic compounds having from 1 to 10 carbon atoms that are known to the person skilled in the art, such as thiophenyl, pyridyl, furanyl, pyranyl, thiazolyl, pyrrolyl, oxazolyl, isoxazolyl, pyrazolyl, imidazolyl, 1,2,3-triazolyl, 1,2,4-triazolyl, benzofuranyl, thianaphthenyl, dibenzofuranyl, indolyl, benzimidazolyl, indazolyl, quinolyl, isoquinolyl; the heteroaryl group can, moreover, carry further substituents. Suitable substituents are hydrogen, halogen, nitro, $C_1$–$C_{10}$-alkoxy or $C_1$–$C_{10}$-alkyl, $C_1$–$C_{10}$-heteroaryl, as well as $C_6$–$C_{14}$-cycloalkyl or $C_6$–$C_{14}$-aryl, such as 2,4-dimethylfuran-3-yl, N-methyl-2-phenyl-pyrrol-4-yl.

$C_1$–$C_{10}$-alkoxy is to be understood as meaning all linear or branched alkoxy radicals having from 1 to 10 carbon atoms that are known to the person skilled in the art, such as methoxy, ethoxy, n-propoxy, isopropoxy, n-butoxy, isobutoxy, tert-butoxy, n-pentoxy, isopentoxy, neopentoxy and hexyloxy, heptyloxy, octyloxy, nonyloxy and decyloxy, which radicals may in turn be substituted.

$C_1$–$C_{10}$-alkyl is to be understood as meaning all linear or branched alkyl radicals having from 1 to 10 carbon atoms that are known to the person skilled in the art, such as methyl, ethyl, n-propyl, isopropyl, n-butyl, isobutyl, tert-butyl, n-pentyl, isopentyl, neopentyl and hexyl, heptyl, octyl, nonyl and decyl, which radicals may in turn be substituted. Suitable substituents are hydrogen, halogen, nitro, hydroxyl or $C_1$–$C_{10}$-alkyl, as well as $C_6$–$C_{14}$-cycloalkyl or $C_6$–$C_{14}$-aryl, such as benzoyl, trimethylphenyl, ethylphenyl, chloromethyl, chloroethyl and nitromethyl.

$C_6$–$C_{14}$-cycloalkyl is to be understood as meaning all mono- or poly-nuclear cycloalkyl radicals having from 6 to 14 carbon atoms that are known to the person skilled in the art, such as cyclohexyl, cycloheptyl, cyclooctyl and cyclononyl, or partially or completely hydrogenated fluorenyl, which radicals may, in turn, be substituted. Suitable substituents are hydrogen, halogen, nitro, $C_1$–$C_{10}$-alkoxy or $C_1$–$C_{10}$-alkyl, as well as $C_6$–$C_{12}$-cycloalkyl or $C_6$–$C_{12}$-aryl, such as methylcyclohexyl, chlorocyclohexyl and nitrocyclohexyl.

As already mentioned, the monoanionic ligands can also be bonded in the form of chelating ligands to one another and/or or the imide.

It is, of course, also possible to introduce further neutral ligands, such as, for example, tetrahydrofuran, 1,2-dimethoxyethane, phosphines, diphosphines, imines, diimines, into the ligand structure of the vanadium-imido-phosphoraneiminato compound. Such compounds containing neutral ligands are expressly included in the present invention. Those neutral ligands can also be bonded to the substituents of the imide group and/or of the phosphoraneiminato group and/or to the groups X, Y.

Preferred monoanionic ligands are halogen, $C_1$–$C_{10}$-alkoxy, $C_6$–$C_{14}$-aryloxy and amido groups. Halogen and $C_1$–$C_{14}$-aryloxy groups are more preferred.

Preferred structures of the vanadium-imido-phosphoraneiminato compounds according to the present invention are:

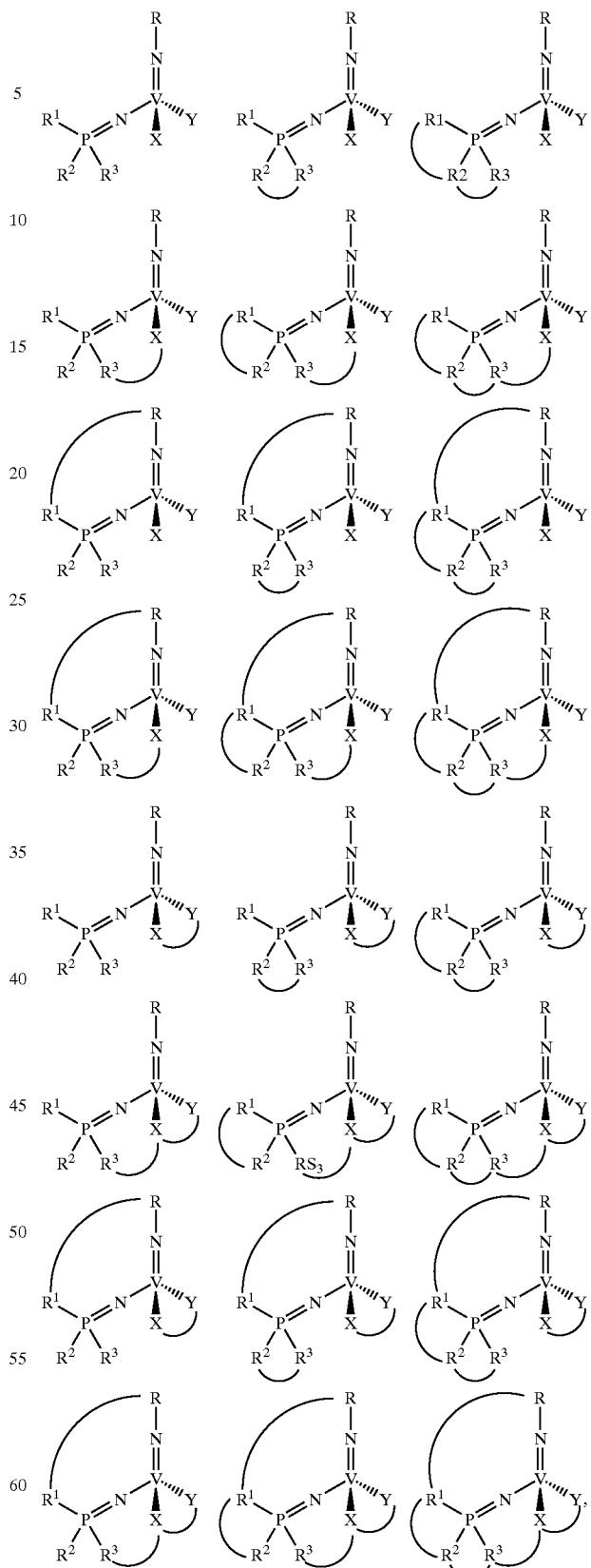

The present invention also provides compositions containing vanadium-imido-phosphoraneiminato compounds and an organometallic compound of group 1, 2, 12 or 13 of the periodic system of the elements according to IUPAC 1985, at least one hydrocarbon group being bonded directly to the metal atom via a carbon atom.

Preferred organometallic compounds are compounds of aluminum, sodium, lithium, zinc and magnesium. Compounds of aluminum are more preferred.

The hydrocarbon group bonded to the metal atom is preferably a $C_1$–$C_{10}$-alkyl group. Examples are amylsodium, butyllithium, diethylzinc, butylmagnesium chloride, dibutylmagnesium. Suitable aluminum compounds are especially trialkylaluminum compounds, alkylaluminum hydrides, such as, for example, diisobutylaluminum hydride, alkylalkoxyaluminum compounds, alkylaryloxyaluminum compounds, aluminoxanes and halogen-containing aluminum compounds, such as, for example, diethylaluminum chloride, diisobutylaluminum chloride, ethylaluminum chloride or ethylaluminum sesquichloride. It is also possible to use mixtures of those components.

The molar ratio between the organometallic compound and the vanadium can be varied within wide limits. In general, it will vary in the range from 1:1 to 5000:1. The range from 1:1 to 500:1 is preferred. The range from 2:1 to 100:1 is more preferred.

The composition is suitable as a catalyst. The present invention relates also to that use. The compound is suitable especially as a catalyst for the polymerization of olefins, especially for ethylene/propylene or ethylene/α-olefin copolymerization and the terpolymerization of those monomers with dienes.

The catalyst can be modified by additives known to the person skilled in the art that increase the productivity of the catalyst and/or alter the properties of the resulting polymer.

As activity-increasing additives, there are preferably used halogen-containing compounds, especially halogen-containing hydrocarbons. Said hydrocarbons can contain further heteroatoms, such as oxygen, nitrogen, phosphorus and sulfur. Particular preference is given to compounds that contain only a little halogen (from 1 to 2 atoms per molecule), because the halogen concentration in the polymer can thus, be kept low. Alkyl and alkoxyalkyl esters of phenyl-mono- and -di-chloroacetic acid as well as diphenyl-chloro-acetic acid are most preferred.

Further suitable activity-increasing additives are Lewis acids, such as, for example, $AlCl_3$, $BCl_3$ or $SiCl_4$, or Lewis bases, such as esters, amines, ammonia, ketones, alcohols, ethers.

Express mention is also made of mixtures of the mentioned activity-increasing additives.

It may be advantageous to apply the catalyst system according to the present invention to a support.

There are used as support materials preferably particulate, organic or inorganic solids whose pore volume is from 0.1 to 15 ml/g, preferably from 0.25 to 5 ml/g, whose specific surface area is greater than 1 $m^2/g$, preferably from 10 to 1000 $m^2/g$ (BET), whose particle size is from 10 to 2500 μm, preferably from 50 to 1000 μm, and which can be suitably modified at their surface.

The specific surface area is determined in the conventional manner according to DIN 66 131, the pore volume is determined by the centrifugation method according to McDaniel, J. Colloid Interface Sci. 1980, 78, 31, and the particle size is determined according to Cornillaut, Appl. Opt. 1972, 11, 265.

The following may be mentioned as examples of suitable inorganic solids: silica gels, precipitated silicas, clays, alumosilicates, talcum, zeolites, carbon black, inorganic oxides, such as, for example, silicon dioxide, aluminum oxide, magnesium oxide, titanium dioxide, inorganic chlorides, such as, for example, magnesium chloride, sodium chloride, lithium chloride, calcium chloride, zinc chloride, or calcium carbonate. The above-mentioned inorganic solids, which meet the above-mentioned specification and therefore, are particularly suitable for use as support materials, are described in greater detail, for example, in Ullmanns Enzyklopädie der technischen Chemie, Volume 21, p. 439 ff (silica gels), Volume 23, p. 311 ff (clays), Volume 14, p. 633 ff (carbon blacks) and Volume 24, p. 575 ff (zeolites).

As organic solids there are suitable powdered, polymeric materials, preferably in the form of free-flowing powders, having the above-mentioned properties. There may be mentioned by way of example, without limiting the present invention: polyolefins, such as, for example, polyethylene, polypropylene, polystyrene, polystyrene-co-divinylbenzene, polybutadiene, polyethers, such as, for example, polyethylene oxide, polyoxytetramethylene, or polysulfides, such as, for example, poly-p-phenylene sulfide. Particularly suitable materials are polypropylene, polystyrene or polystyrene-co-divinylbenzene. The mentioned organic solids, which meet the above-mentioned specification and therefore, are particularly suitable for use as support materials, are described in greater detail, for example, in Ullmanns Enzyklopädie der technischen Chemie, Volume 19, p. 195 ff (polypropylene) and Volume 19, p. 265 ff (polystyrene).

The preparation of the supported catalyst system can take place in a wide temperature range. In general, the temperature is between the melting point and the boiling point of the inert solvent mixture. The reaction is usually carried out at temperatures of from −50 to +200° C., preferably from −20 to 100° C., more preferably from 20 to 60° C.

The invention relates also to a process for the homo- or co-polymerization of olefins, preferably ethylene, propylene, isobutene, 1-butene, 2-butene, 1-hexene, 1-octene, 4-methyl-1-pentene, unsaturated alicyclic compounds such as, for example, cyclopentene, norbornene, and to a process for the copolymerization of those monomers with one or more dienes, preferably ethylidene norbornene, vinyl norbornene, dicyclo-pentadiene, 1,4-hexadiene.

The polymerization is preferably carried out by bringing the α-olefins into contact with the catalyst system according to the present invention in solution in suitable solvents, in gaseous form, in finely distributed liquid form or in suspension in a liquid diluent. The catalysts are generally used in amounts in the range from $10^{-10}$ to $10^{-1}$ mol % per mole of monomer.

It is possible to mix with the gaseous, liquid or atomized monomers further gases or finely divided liquids, which serve either for dilution, for atomization or for the dissipation of heat.

The examples which follow are intended to illustrate the present invention and the implementation of homo- and co-polymerization processes catalyzed therewith.

EXAMPLES

All the syntheses listed were carried out under an argon atmosphere.

Unless described otherwise, all the chemicals used are commercial products of Acros, Aldrich, Avocado, Fluka or Merck-Schuchardt.

Dichlorophenylacetic acid ethyl ester was synthesized as specified in the literature (EP 75 355, page 3, Example II).

Example 1

Comparative Example
Synthesis of (2,4,6-Cl$_3$Ph)-N=VCl$_3$

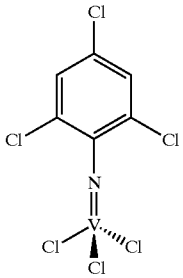

3.65 g (2 ml, 21.1 mmol) of VOCl$_3$ in 20 ml of toluene are added dropwise at room temperature to 6.64 g (27.4 mmol) of 2,4,6-trichlorophenyl-sulfinylamine in 40 ml of toluene. The reaction mixture spontaneously turns dark-green in color. After 30 minutes stirring, volatile constituents are removed in vacuo, and the residue is digested three times using 20 ml of pentane each time and is stored for 24 hours at −80° C. Portions that are insoluble in pentane are filtered off, and the filtrate is concentrated to dryness in order to obtain the complex.

Yield: 6.3 g (85%).

.C; 20.79 (calc. 20.49); H: 0.57 (calc. 0.63); N: 4.02 (calc. 3.98).

.$^1$H-NMR (200 MHz, C$_6$D$_6$): 6.24 (s, 2H, Ar—H$_{meta}$) ppm.

$^{13}$C-NMR (50 MHz, C$_6$D$_6$): 128.3 (Ar—C$_{meta}$), 135.9, 136.7 (Ar—C$_{ortho}$+C$_{para}$) ppm.

$^{51}$V-NMR (131 MHz, C$_6$D$_6$): 276.6 ppm.

IR (Nujol): 1551 vs, 1522 m, 1512 m, 1306 m, 1206 m, 1190m, 1153 s, 1084 m, 1063 w, 972 w, 876 w, 858 s, 839 w, 820 s, 806 m, 729 w, 721 w, 710 w, 696 w, 669 w, 611 w, 575 w, 529 w, 484 w, 453 s cm$^{-1}$ EI-MS: m/z=352 (M$^+$, 12%), 196 (C$_6$H$_2$Cl$_3$N$^+$, 100%), 158 (VCl$_3$$^+$, 28%)

Example 2

Synthesis of (2,4,6-Cl$_3$Ph)-N=VCl$_2$(N=PnBu$_3$)

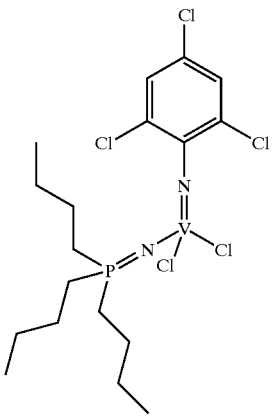

0.82 g (2.84 mmol) of N-trimethylsilyl-tri(n-butyl)-iminophosphorane (synthesis according to C. Birkhofer, S. M. Kiun, Chem. Ber. 97.2 (1964), 2100) is added at −50° C., with stirring, to a solution of 1.00 g (2.84 mmol) of (2,4,6-Cl$_3$Ph)-N=VCl$_3$ in 100 ml of toluene. The reaction solution initially turns olive-green in color. After 2 hours, the reaction mixture is warmed to room temperature and the solution, which is now brownish-red, is then stirred for 60 minutes in the absence of light. After removal of the solvent, the oily crude product is taken up in 2 ml of hexane and stored for 48 hours at −80° C. The resulting blue solid is filtered off and dried under a high vacuum.

Yield: 1.13 g (74%), microcrystalline blue-violet solid.
C$_{18}$H$_{29}$Cl$_5$N$_2$PV (532.62).

| calc.: | C 40.59 | H 5.49 | N 5.26 |
| found: | C 41.20 | H 5.68 | N 5.47 |

$^1$H-NMR (300 MHz, CDCl$_3$): δ=0.83 (t, 9H, $^3$J$_{HH}$=14.6 Hz, CH$_2$—CH$_3$), 1.24–1.32 (m, 4H, CH$_2$—CH$_2$—CH$_3$), 1.84–1.88 (m, 2H, P—CH$_2$—CH$_2$) Ar—H$_{meta}$) ppm.

$^{13}$C-NMR (75 MHz, CDCl$_3$): δ=13.7 (—CH$_3$), 24.5 (CH$_2$—CH$_2$), 26.48 (d, P—CH$_2$—CH$_2$).

IR (Nujol): ν=1763 w, 1643 w, 1556 w, 1282 m, 1140 s, 1103 s, 1072 s, 979 m, 912 m, 883 w, 866 w, 821 w, 800 cm$^{-1}$.

Example 3

Synthesis of (2,6-iPr$_2$Ph)-N=VCl$_3$

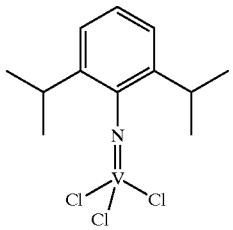

(2,6-iPr$_2$Ph)-N=VCl$_3$ is prepared as specified in the literature (D. D. Devore et al. J. Am. Chem. Soc. Vol. 109 (1987), 748–16).

Synthesis of (2,6-iPr$_2$Ph)-N=VCl$_2$(N=PnBu$_3$)

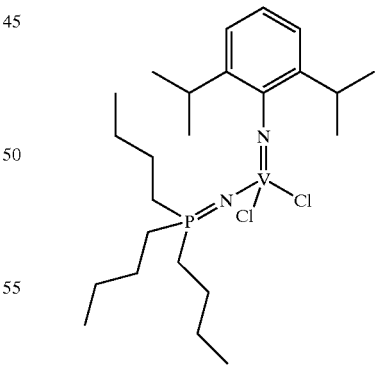

870 mg (3.00 mmol) of N-trimethylsilyl-tri(tert-butyl)-iminophosphorane (synthesis according to C. Birkhofer, S. M. Kiun, Chem. Ber. 97.2 (1964), 2100) are dissolved in 40 ml of toluene and cooled to −20° C., and a solution of 1.00 g (3.00 mmol) of [(2,6-iPr$_2$Ph)-N=VCl$_3$] in 20 ml of toluene is added thereto. The reaction solution turns reddish-brown in color within 2 minutes. After 30 minutes, the reaction mixture is warmed to room temperature, stirred for a further 5 minutes and filtered over thoroughly heated Celite, and the filtrate is greatly concentrated. The wax-like crude product is taken up in 5 ml of pentane and stored for 24 hours at −80° C. The resulting solid is filtered off and dried under a high vacuum.

Yield: 1.76 g (74%), reddish-brown amorphous solid.
Yield: 722 mg (85%).
red amorphous solid
$C_{24}H_{44}Cl_2N_2PV$ (513.45) $C_{24}H_{44}Cl_2N_2PV \times C_7H_8$ (605.59).

| calc.: | C 56.14 | H 8.64 | N 5.46 |
| --- | --- | --- | --- |
| found: | C 56.32 | H 8.48 | N 5.12 |

EI-MS: m/z=513 (M$^+$, 14%), 216.3 (NP"Bu$_3$, 72%).

Example 4

Comparative Example
Synthesis of VOCl$_2$(N=PnBu$_3$)

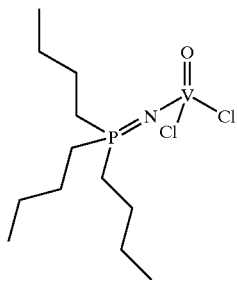

1.64 g (5.68 mmol) of N-trimethylsilyl-tri(n-butyl)-iminophosphorane (synthesis according to C. Birkhofer, S. M. Kiun, Chem. Ber. 97.2 (1964), 2100) are added at −30° C., with stirring, to a solution of 0.98 g (5.68 mmol) of VOCl$_3$ in 50 ml of toluene. The reaction solution initially turns deep-red in color. After one hour, the reaction mixture is warmed to room temperature and the solution, which is now yellow, is then stirred for 60 minutes. After concentration of the solvent to 10 ml, the solution is covered with a layer of 5 ml of hexane and stored for 48 hours at −80° C. The resulting deep-yellow solid is filtered off and dried under a high vacuum.

Yield: 1.57 g (78%), crystalline yellow needles.
$C_{12}H_{27}Cl_2N_1PV$ (354.17).

| calc.: | C 40.70 | H 7.68 | N 3.95 |
| --- | --- | --- | --- |
| found: | C 40.82 | H 4.48 | N 7.84 |

$^1$H-NMR (300 MHz, CDCl$_3$): δ=0.94 (t, 9H, $^3J_{HH}$=14.3 Hz, CH$_2$—C$\underline{H}_3$), 1.41–1.61 (m, 4H, C$\underline{H}_2$—C$\underline{H}_2$—CH$_3$), 2.16–2.30 (m, 2H, P—C$\underline{H}_2$—CH$_2$) ppm.

$^{13}$C-NMR (75 MHz, CDCl$_3$): δ=13.8 (—$\underline{C}$H$_3$), 24.2 ($\underline{C}$H$_2$—$\underline{C}$H$_2$), 25.38 (d, P—$\underline{C}$H$_2$—CH$_2$).

$^{31}$P-NMR (50 MHz, CDCl$_3$): δ=49.2–53.3 (V-P coupling).

IR (Nujol): ν=1671 w, 1555 w, 1524 w, 1461 m, 1082 m, 985 cm$^{-1}$.

EI-MS: m/z=317.3 (M$^+$—Cl, 11.6%), 216.3 (NP"Bu$_3$, 100%).

Example 5

Synthesis of (2,4,6-Cl$_3$Ph)-N=VCl$_2$(N=PtBu$_3$)

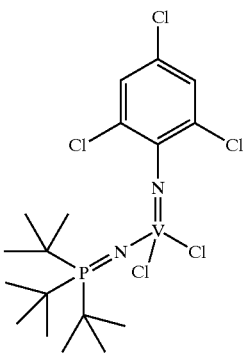

0.82 g (2.84 mmol) of N-trimethylsilyl-tri(tert-butyl)-iminophosphorane (synthesis according to H. Schmidbauer, G. Blaschke, Z. Naturforsch. 33b, (1978) 1556) in 50 ml of toluene is slowly added dropwise (dropping rate: approx. 15 min.) at −50° C., with stirring, to a solution of 1.00 g (2.84 mmol) of (2,4,6-Cl$_3$Ph)-N=VCl$_3$ in 100 ml of toluene. The reaction solution turns from light-red to green in color. After 4 hours, the reaction mixture is warmed to room temperature and the solution, which has in the meantime turned bluish-green, is then stirred for 2 hours. After removal of the solvent, the oily blue crude product is taken up in 4 ml of hexane and stored for 48 hours at −80° C. The resulting deep-blue solid is filtered off and dried under a high vacuum.

Yield: 1.32 g (86%), microcrystalline blue-violet solid $C_{18}H_{29}Cl_5N_2PV$ (532.62)

| calc.: | C 40.59 | H 5.49 | N 5.26 |
| --- | --- | --- | --- |
| found: | C 40.18 | H 5.81 | N 5.50 |

$^1$H-NMR (300 MHz, CDCl$_3$): δ=1.53 (d, $^3J_{HP}$=14.4 Hz, C—C$\underline{H}_3$), 7.159 (s, 2H, Ar—$\underline{H}_{meta}$) ppm.

$^{13}$C-NMR (75 MHz, CDCl$_3$): δ=29.5 ($\underline{C}$—CH$_3$), 43.0 (d, $\underline{C}$—CH$_3$), 127.3 (Ar).

IR (Nujol): ν=1734 w, 1575 w, 1523 w, 1261 m, 1111 s, 1084 s, 1020 s, 974 m, 937 m, 873 w, 862 w, 817 w, 800 cm$^{-1}$.

Example 6

Synthesis of (2,6-iPr$_2$Ph)-N=VCl$_2$ (N=PtBu$_3$)

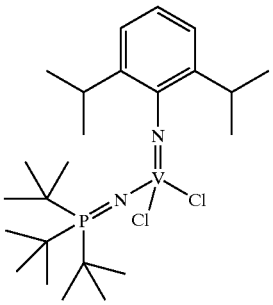

(2,6-iPr$_2$Ph)-N=VCl$_3$ is prepared as specified in the literature (D. D. Devore et al. J. Am. Chem. Soc. Vol. 109 (1987), 748–16).

435 mg (1.50 mmol) of N-trimethylsilyl-tri(tert-butyl)-iminophosphorane (synthesis according to H. Schmidbauer, G. Blaschke, Z. Naturforsch. 33b, (1978) 1556) are dissolved in 10 ml of toluene and cooled to 0° C., and a solution of 500 mg (1.50 mmol) of [V(Ndip)Cl$_3$] in 10 ml of toluene is added thereto. The reaction solution turns reddish-brown in color within 5 minutes. After 10 minutes, the reaction mixture is warmed to room temperature, stirred for a further 5 minutes and filtered over thoroughly heated Celite, and the filtrate is greatly concentrated. The wax-like crude product is taken up in 5 ml of pentane and stored for 24 hours at −80° C. The resulting solid is filtered off and dried under a high vacuum.

Yield: 722 mg (85%), red amorphous solid.

$C_{24}H_{44}Cl_2N_2PV$ (513.45) $C_{24}H_{44}Cl_2N_2PV$ x $C_7H_8$ (605.59).

| calc.: | C 61.48 | H 8.65 | N 4.63 |
|---|---|---|---|
| found: | C 61.28 | H 8.54 | N 4.89 |

$^1$H-NMR (200 MHz, C$_6$D$_6$): δ=1.15 (s (br), tot. 39H, CH(C$\underline{H}_3$)$_2$ and C(C$\underline{H}_3$)$_3$), 4.32 (sep, 2H, $^3J_{HH}$=6.7 Hz, C$\underline{H}$(CH$_3$)$_2$), 7.10–7.16 (m, 3H, $\underline{H}_{ar}$) ppm.

$^{13}$C-NMR (50 MHz, C$_6$D$_6$): δ=23.9 (CH($\underline{C}$H$_3$)$_2$), 29.4 ($\underline{C}$H(CH$_3$)$_2$), 30.2 (PC($\underline{C}$H$_3$)$_3$), 41.3 (P$\underline{C}$(CH$_3$)$_3$), 122.5 (Ar—$\underline{C}_{meta}$), 128.9 (Ar—$\underline{C}_{para}$), 134.7 (Ar—$\underline{C}_{ortho}$) ppm.

$^{31}$P-NMR (81 MHz, C$_6$D$_6$): δ=36.1 ppm.

$^{51}$V-NMR (131 MHz, C$_6$D$_6$): δ=−363.8 ppm.

IR (Nujol): ν=1709 m, 1655 m, 1619 s, 1573 s, 1486 m, 1332 w, 1265 vs, 1179 w, 1151 w, 1076 m, 1026 w, 992 m, 970 w, 942 m, 896 w, 875 w, 845 w, 811 s, 739 vs, 704 s, 629 w cm$^{-1}$.

EI-MS: m/z=513 (M$^+$, 8%), 297 (C$_{12}$H$_{17}$NVCl$_2$$^+$, 26%), 77 (C$_6$H$_5$$^+$, 100%).

Example 7

Comparative Example

Synthesis of VOCl$_2$(N═PtBu$_3$)

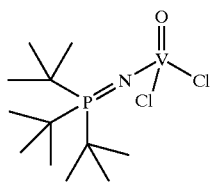

The synthesis of VOCl$_2$(N═PtBu$_3$) was carried out as described in WO 00/00525 (Example A.6, page 18, lines 22–32).

Example 8

Preparation of (2,4,6-Cl$_3$Ph)-N═VCl$_2$(N═PPh$_3$)

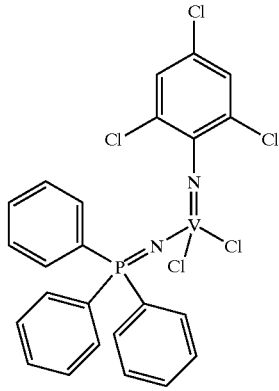

A solution of 0.99 g (2.84 mmol) of N-trimethylsilyl-triphenyl-iminophosphorane (synthesis according to L. Birkhofer, S. M. Kim, Chem. Ber. 97 (1964), 2100; H. Schmidbaur, W. Wolfsberger, Chem. Ber. 100 (1967), 1000; W. Buchner, W. Wolfsberger, Z. Naturforsch. 29b (1974), 328) in 50 ml of toluene is added at −50° C., with stirring, to a solution of 1.00 g (2.84 mmol) of (2,4,6-Cl$_3$Ph)-N═VCl$_3$ in 100 ml of toluene. The reaction mixture initially turns deep-green in color. After 30 minutes, it is heated to room temperature and the solution, which is now brownish-red, is then stirred for 60 minutes in the absence of light. After concentration of the solvent to about 40 ml, the solution is covered with a layer of 40 ml of hexane and stored for 48 hours at −80° C. The resulting dark-brown solid is filtered off and dried under a high vacuum.

Yield: 1.14 g (68%), amorphous, dark-brown solid.

$C_{24}H_{17}Cl_5N_2PV$ (592.59).

| calc.: | C 48.64 | H 2.89 | N 4.73 |
|---|---|---|---|
| found: | C 46.22 | H 2.77 | N 4.54 |

$^1$H-NMR (200 MHz, C$_6$D$_6$): δ=6.90–6.98 (m, 3H, Ph$\underline{H}_{meta, para}$), 7.159 (s, 2H, Ar—$\underline{H}$meta), 7.77–7.87 (m, 2H, Ph-$\underline{H}_{ortho}$) ppm.

$^{13}$C-NMR (50 MHz, C$_6$D$_6$): 127.9 (arylimido), 128.8 (Ph-$\underline{C}^{3,5}$), 131.5 (Ph-$\underline{C}^4$), 133.2 (Ph-$\underline{C}^{2,6}$), 136.4 (d, $^1J_{PC}$= 98.9 Hz, Ph-$\underline{C}^1$) ppm.

IR (Nujol): ν=1761 w, 1635 w, 1471 w, 1212 m, 1135 s, 1109 s, 1068 s, 954 m, 902 m, 881 w, 834w, 811 w, 803 cm$^{-1}$.

EI-MS: m/z=277.8 (39%), 246.1 (64%).

Example 9

Preparation of (2,6-iPr$_2$Ph)-N=VCl$_2$(N=PPh$_3$)

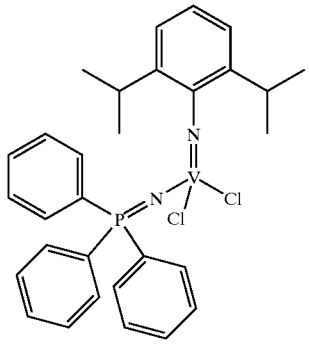

(2,6-iPr$_2$Ph)-N=VCl$_3$ is prepared as specified in the literature (D. D. Devore et al. J. Am. Chem. Soc. Vol. 109 (1987), 748–16).

A solution of 0.99 g (2.84 mmol) of N-trimethylsilyl-triphenyl-iminophosphorane (synthesis according to L. Birkhofer, S. M. Kim, Chem. Ber. 97 (1964), 2100; H. Schmidbaur, W. Wolfsberger, Chem. Ber. 100 (1967), 1000; W. Buchner, W. Wolfsberger, Z. Naturforsch. 29b (1974), 328) in 50 ml of toluene is added at −50° C., with stirring, to a solution of 0.94 g (2.84 mmol) of (2,6-iPr$_2$Ph)-N=VCl$_3$ in 100 ml of toluene. The reaction mixture initially turns deep-green in color. After 10 minutes, it is heated to room temperature, and the deep-red solution is then stirred for 2 hours in the absence of light. After concentration of the solvent to about 20 ml, the solution is covered with a layer of 20 ml of hexane and stored for 48 hours at −80° C. The resulting dark-green solid is filtered off and dried under a high vacuum.

Yield: 1.27 g (78%), amorphous, dark-green solid. C$_{30}$H$_{32}$Cl$_2$N$_2$PV (573.42).

| | | | |
|---|---|---|---|
| calc.: | C 62.84 | H 5.62 | N 4.89 |
| found: | C 64.42 | H 5.44 | N 4.11 |

IR (Nujol): ν=1757 w, 1628 w, 1463 w, 1202 m, 1138 s, 1111 s, 1057 s, 957 w, 912 m, 883 w, 812 w cm$^{-1}$.

EI-MS: m/z=277.8 (36%), 225.1 (24%)

Example 10

Comparative Example

Preparation of VOCl$_2$(N=PPh$_3$)

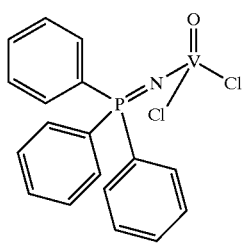

The synthesis of VOCl$_2$(N=PPh$_3$) was carried out as described by R. Choukroun et al. in Trans. Met. Chem. 4 (1979), 249–251.

Example 11

Ethylene/propylene Copolymerization

The apparatus, adjusted to a temperature of 40° C. with a thermostat, is evacuated to $5*10^{-2}$ for 30 minutes. Purified propylene is then introduced to a pressure of 1.5 bar. 40 ml of hexane, which has been rendered absolute, and 0.408 mmol (18.5 eq) of a 15% solution of ethylaluminum sesquichloride in heptane are introduced into the autoclave in a propylene countercurrent. The apparatus is then closed under a propylene atmosphere in order to fill a pressure syringe with 50 ml of hexane and 0.096 mmol (4.4 eq) of dichlorophenylacetic acid ethyl ester in a propylene countercurrent.

0.022 mmol (1.0 eq) of the vanadium precursor compound dissolved in 30 ml of hexane is then introduced into a stirrer vessel. The hexane solution is saturated for 15 minutes with propylene at 3.7 bar. After shutting off the supply of propylene, the overall pressure is adjusted to 5.5 bar with purified ethylene. The reaction takes place at 40° C. and is started by injection of the reactivator using the pressure syringe. Stirring is carried out by means of an anchor stirrer under a constant ethylene pressure at 5.5 bar and at 1000 rpm.

After 10 minutes, the reaction is terminated by the dropwise addition of the mixture into hydrochloric acid-containing methanol. The polymer precipitate is washed with ethanol and then dried for 10 hours at 50° C., and the yield is determined.

Table 1:

Results of the ethylene/propylene copolymerization by vanadium-imido-phosphoraneiminato catalysts.

TABLE 1

| Catalyst | Yield [g] |
|---|---|
| VOCl$_2$(N = P$^n$Bu$_3$) | 5.90 |
| (2,6-iPr$_2$Ph)-N = VCl$_2$(N = P$^n$Bu$_3$) | 9.33 |
| (2,4,6-Cl$_3$Ph)-N = VCl$_2$(N = P$^n$Bu$_3$) | 11.17 |
| VOCl$_2$(N = P$^t$Bu$_3$) | 5.96 |
| (2,6-iPr$_2$Ph)-N = VCl$_2$(N = P$^t$Bu$_3$) | 9.56 |
| (2,4,6-Cl$_3$Ph)-N = VCl$_2$(N = P$^t$Bu$_3$) | 11.66 |
| VOCl$_2$(N = PPh$_3$) | 3.17 |
| (2,4,6-Cl$_3$Ph)-N = VCl$_2$(N = PPh$_3$) | 7.88 |

Table 1 shows clearly that the novel imido-phosphoraneiminato complexes of vanadium give higher yields of polymer than the analogous vanadyl-phosphoraneiminato complexes.

Example 12

EPDM Synthesis

An autoclave which has been rendered inert is filled with 1500 ml of hexane and 6.0 g of ethylidene norbornene and heated to the polymerization temperature of 40° C. Ethylene and propylene are then introduced in a ratio of 1:19 to a pressure of 7 bar. The catalyst components (0.05 mmol of V component, 1 mmol of ethylaluminum sesquichloride and 0.25 mmol of dichlorophenylacetic acid ethyl ester) are introduced into the reactor simultaneously via pressure burettes, and polymerization is then carried out at a pressure of 7.0 bar. Regulation is effected by the metered addition of ethylene. After half an hour, the test is terminated and the batch is transferred to a container filled with ethanol. The polymer is dried at 80° C. in a vacuum drying cabinet.

Table 2:

Results of the ethylene/propylene/ethylidene norbornene terpolymerization by vanadium catalysts.

TABLE 2

| Catalyst | Yield [g] | E [wt. %] | P [wt. %] | ENB [wt. %] | Tg [° C.] |
|---|---|---|---|---|---|
| O = VCl$_3$ | 25.9 | 46.0 | 44.2 | 9.8 | −46 |
| (2,4,6-Cl$_3$Ph)-N = VCl$_3$ | 31.3 | 48.3 | 42.0 | 9.7 | −46 |
| (2,4,6-Cl$_3$Ph)-N = VCl$_2$(NPPh$_3$) | 38.4 | 50.9 | 39.8 | 9.3 | −48 |

The results show clearly that the novel imido-phosphoraneiminato complexes are not only markedly more active than VOCl$_3$ and the corresponding imido complexes, but also, under the same conditions, produce terpolymers having a changed composition and lower glass transition temperatures.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Vanadium-imido-phosphoraneiminato compounds, which correspond to the general formula $$R-N=VCl_2(NPR^1R^2R^3) \quad (I)$$

or $$R-N=VXY(NPR^1R^2R^3) \quad (II),$$

wherein

R represents a C$_1$–C$_{10}$-alkyl group, a C$_6$–C$_{14}$-aryl group or a C$_1$–C$_{10}$-heteroaryl group, wherein X,Y are each independently of the other different or identical monoanionic ligands which may be bonded to one another and/or to the R group of the imide, or its substituents, and/or to the radicals R$^1$, R$^2$, R$^3$ of the iminophosphorane, or wherein X and/or Y is likewise an iminophosphorane having radicals R$^4$, R$^5$, R$^6$ and R$^7$, R$^8$, R$^9$ wherein R$^1$, R$^2$, R$^3$ and, optionally, R$^4$, R$^5$, R$^6$, R$^7$, R$^8$, R$^9$ are each independently of the others different or identical C$_1$–C$_{10}$-alkyl, C$_6$–C$_{14}$-aryl, C$_1$–C$_{10}$-alkoxy groups which may be bonded to one another and/or to the R group of the imide, or its substituents, and/or to the radicals R$^1$, R$^2$, R$^3$ of the iminophosphorane, or alternatively one or more substituents of the phosphorus are bonded to the phosphorus via heteroatoms selected from N, O, and S.

2. Vanadium-imido-phosphoraneiminato compounds according to claim 1, wherein said compounds correspond to one of the following structures:

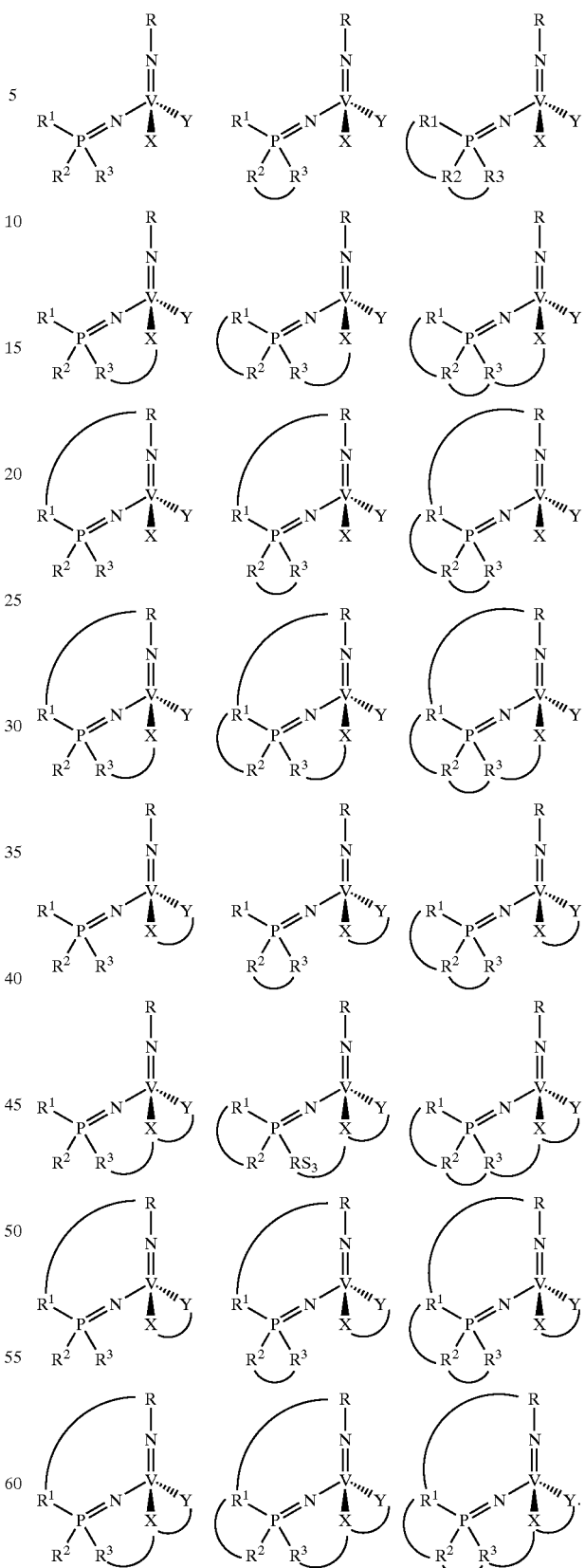

3. A composition comprising vanadium-imido-phosphoraneiminato compounds and an organometallic compound of Groups 1, 2, 12 or 13 of the periodic system of the elements according to IUPAC 1985, wherein at least one hydrocarbon group in said organometallic compound is bonded directly to the metal atom via a carbon atom, wherein said vanadium-imido-phosphoraneiminato compound corresponds to the general formula $$R\text{—}N\text{=}VCl_2(NPR^1R^2R^3) \qquad (I)$$

or $$R\text{—}N\text{=}VXY(NPR^1R^2R^3) \qquad (II),$$

wherein

R represents a $C_1$–$C_{10}$-alkyl group, a $C_6$–$C_{14}$-aryl group or a $C_1$–$C_{10}$-heteroaryl group, wherein X,Y are each independently of the other different or identical monoanionic ligands which may be bonded to one another and/or to the R group of the imide, or its substituents, and/or to the radicals $R^1$, $R^2$, $R^3$ of the iminophosphorane, or wherein X and/or Y is likewise an iminophosphorane having radicals $R^4$, $R^5$, $R^6$ and $R^7$, $R^8$, $R^9$, wherein $R^1$, $R^2$, $R^3$ and, optionally, $R^4$, $R^5$, $R^6$, $R^7$, $R^8$, $R^9$ are each independently of the others different or identical $C_1$–$C_{10}$-alkyl, $C_6$–$C_{14}$-aryl, $C_1$–$C_{10}$-alkoxy groups which may be bonded to one another and/or to the R group of the imide, or its substituents, and/or to the radicals $R^1$, $R^2$, $R^3$ of the iminophosphorane, or alternatively one or more substituents of the phosphorus are bonded to the phosphorus via heteroatoms selected from N, O and S; and an organometallic compound selected from the group consisting of aluminum, sodium, lithium, zinc and magnesium.

* * * * *